United States Patent
Shinomiya

[11] Patent Number: 5,877,507
[45] Date of Patent: Mar. 2, 1999

[54] OPTICAL DETECTION DEVICE AND LIGHTING METHOD WITH VARIED IRRADIATION ANGLE IN OPTICAL DETECTION PROCESS

[75] Inventor: Makoto Shinomiya, Kawasaki, Japan

[73] Assignee: Fujitsu Limited, Kawasaki, Japan

[21] Appl. No.: 890,995

[22] Filed: Jul. 10, 1997

[30] Foreign Application Priority Data

Dec. 25, 1996 [JP] Japan .................................... 8-346030

[51] Int. Cl.$^6$ .................................................. G01N 21/86
[52] U.S. Cl. .................... 250/559.4; 250/216; 356/237.5
[58] Field of Search ........................... 250/559.4, 559.45, 250/216; 356/237.5, 237.3, 430, 431

[56] References Cited

U.S. PATENT DOCUMENTS 4,555,635 11/1985 Yoshida ............................... 250/559.46

*Primary Examiner*—Que T. Le
*Attorney, Agent, or Firm*—Staas & Halsey

[57] ABSTRACT

An optical detection device includes a light source device from which a light beam is irradiated on an object; an image processing unit for receiving a reflected light beam from the object by a camera and producing image data; a half-mirror provided one of between the camera and the object and between the light source device and the object; and a recognition element for carrying out a recognition process of the object based on the image data produced by the image processing unit. An irradiation angle of the light beam from the light source device is continuously varied with respect to the half-mirror, and the light beam from the light source device is always irradiated on the object via the half-mirror.

12 Claims, 11 Drawing Sheets

OPTICAL DETECTION DEVICE AND LIGHTING METHOD WITH VARIED IRRADIATION ANGLE IN OPTICAL DETECTION PROCESS

BACKGROUND OF THE INVENTION

The present invention generally relates to optical detection devices and lighting methods used in optical detection processes. More particularly, the present invention relates to an optical detection device in which recognition and detection of an object is carried out by irradiating a light beam onto the object, receiving a reflected light beam from the object using a camera such as a CCD to produce image data, and processing the image data, and a lighting method used for such an optical detection device.

Recently, a number of manufacturing processes are automated and, accordingly, a need for automated detection means of a product has been increased. In a process of manufacturing semiconductor elements, it becomes possible to carry out a control of wafers by recognizing an ID provided on the surface of each wafer using such automated detection means. Thus, yields of semiconductor elements may be increased and a production efficiency may be improved by analysis based on the information obtained. For this reason, the ID recognition techniques in the semiconductor manufacturing processes have become increasingly important.

When an examination (recognition process) of an object is performed in a conventional manner, using image processing, as shown in FIGS. 1 and 2, a light beam from a light source device 1 is irradiated onto an object (in this case an ID 5 provided on a semiconductor wafer 4), a reflected light beam from the object is received by using a CCD 2, which is a camera means, to produce image data, and the image data is processed using an image processing apparatus 3.

There are two main lighting methods used in an optical detecting process—one is a coaxial lighting method shown in FIG. 1 in which a light beam is irradiated from the same axis as a camera axis and the other is a non-coaxial lighting method shown in FIG. 2 in which a light beam is irradiated diagonally. In the coaxial lighting method shown in FIG. 1, since the light source device 1 and the CCD 2 cannot be located at the same position, a half-mirror 6 is provided so that the axis of the light beam from the light source device 1 is superimposed with the axis of the CCD 2.

Usually, one of the above two lighting methods which is appropriate for examining an object is selected. This is because a better contrast or higher quality of an image suitable for an optical detection process may be obtained using one over the other. Also, both the coaxial and the non-coaxial lighting methods may be used at the same time for image processing on some occasions.

When the recognition of the ID 5 provided on the semiconductor wafer 4 is performed, both the coaxial and the non-coaxial lighting methods shown in FIGS. 1 and 2, respectively, may be used. Note that the ID 5 is formed before circuits are fabricated on the wafer 4. Also, the ID 5 is practically formed by shaving the surface of the wafer 4 using a laser beam. Thus, the ID 5 has a groove shape, and hence may be recognized optically.

However, when an examination is conducted on objects of varying shape in the above-mentioned optical detection process, since the shape of the objects varies, it is necessary to irradiate a light beam from various directions. In such a case, it is necessary to carry out irradiation operations of a light beam from various directions and select the best lighting mode.

In the above-mentioned coaxial and non-coaxial lighting methods or the combination thereof, however, the configuration of the lighting device tends to be complicated and the cost as well as the size of the optical detection device may be increased. Also, it is not possible to continuously change the irradiation angle of the light beam using the conventional non-coaxial lighting method (or device). That is, the irradiation angle must be changed using certain intervals (5° interval, for instance). For this reason, the angles of the light irradiation which may be used are limited even if a plurality of non-coaxial lighting devices are employed. Hence, there is a danger that an optical detection process may not be performed under good conditions.

Also, when the ID 5 formed on the wafer 4 is detected using the system shown in FIGS. 1 and 2, it is necessary to carry out the detection process by irradiating a light beam from various directions by combining the coaxial and the non-coaxial systems since the structure of each ID 5 may be different depending on the method used for the ID 5 formation or the manufacturing process of semiconductors. However, if the irradiation angle of the light beam may not be varied continuously in the non-coaxial system, there is a danger that the best irradiating angle may not be used, and hence it is difficult to perform the light irradiation process for the ID 5 under the best conditions.

In order to solve the above-mentioned problem, the depth of the groove of the ID 5 formed on the wafer 4 may be deepened so that a larger contrast may be obtained from the reflective light. However, since an extremely fine process is performed in the wafer process, debris of the wafer from the groove portion after the irradiation of the laser beam affects the processes which follow. The deeper the depth of the groove portion, the larger the scale of the affection.

That is, the debris remains in the portion which is assigned to the circuit portion and causes problems. Thus, it is desirable that the depth of the groove of the ID 5 be as shallow as possible. However, a good image contrast is hard to obtain from the shallow groove using the conventional coaxial lighting system or non-coaxial lighting system, and hence it becomes difficult to accurately detect the ID 5.

SUMMARY OF THE INVENTION

Accordingly, it is a general object of this invention to provide optical detection devices and lighting methods used in optical detection processes in which the above-mentioned problems are eliminated.

Another object of this invention is to provide an optical detection device and a lighting method used in optical detection processes by which excellent processed image having good contrast may be obtained when carrying out an optical detection process for objects of varying shape, especially for an ID formed on a wafer.

The objects described above are achieved by an optical detection device comprising: a light source device from which a light beam is irradiated on an object; an image processing means for receiving a reflected light beam from the object by a camera and producing image data; a half-mirror provided one of between the camera and the object and between the light source device and the object; and a recognition means for carrying out a recognition process of the object based on the image data produced by the image processing means, wherein an irradiation angle of the light beam from the light source device is continuously varied with respect to the half-mirror, and the light beam from the light source device is always irradiated on the object via the half-mirror.

According to the above optical detection device, the light source device irradiates a light beam on the object and the image data are produced by receiving the reflected light beam from the object using the camera means. Also, the half-mirror may be provided between the camera means and the object so that the axis of the light beam from the light source device is aligned with a camera axis. Moreover, the recognition means carries out a recognition process of the object based on the image data produced by the image processing means.

In the above-mentioned configuration of the optical detection device, since an irradiation angle of the light beam from the light source device may be continuously varied with respect to the half-mirror, an irradiation angle of the light beam with respect to the object may also be continuously changed. Accordingly, it becomes possible to obtain an image of an object of varying shape with high contrast since the irradiation of the light beam may be continuously varied with respect to the object using a single light source device. Thus, an optical detection process may be performed with high accuracy. Also, since an image of high contrast is obtained using the single light source device, the structure of the light source device may be simplified.

Moreover, since the optical detection device is constructed so that the light beam, which is emitted from the light source device and reflected by or transmitted through the half-mirror, is always irradiated on the object, the light beam is not shifted from the object when the irradiation angle of the light beam is continuously changed.

The objects described above are also achieved by the optical detection device, wherein the object is a groove portion formed on a semiconductor wafer.

According to the above optical detection device, since an image of high contrast can be obtained by continuously changing the irradiation angle as mentioned above, it is possible to detect the groove portion even if the depth of the groove is relatively shallow. Thus, the amount of debris which is produced at the time of the groove formation may be reduced, and the yield of various circuits formed on the semiconductor wafer after the formation of the groove portion may be increased.

The objects described above are also achieved by the optical detection device, wherein the light source device, the half-mirror, and the object are positioned so as to satisfy an equation $L_0=L_1$ where $L_0$ is the distance between the half-mirror and a rotation center of the light source device, and $L_1$ is the distance between the half-mirror and the object.

According to the above optical detection device, since the light source device, the half-mirror, and the object are provided so as to satisfy the equation $L_0=L_1$, the light beam emitted from the light source device may always be irradiated on the object.

As mentioned above, since the irradiation position may be determined by simply defining the position of the light source device, the half-mirror, and the object so as to satisfy the equation $L_0=L_1$, it is easy to carry out the irradiation position determining process.

The objects described above are also achieved by the optical detection device, wherein the light source device is in connection with a light source via an optical fiber, and the light source device is provided with an optical system makes a light beam supplied via the optical fiber a parallel beam.

According to the above optical detection device, since the light source device is in connection with the light source via the optical fiber which is flexible, it is easy to move the position of the light source device from which the light beam is emitted.

Also, since the optical system which is capable of making a light beam supplied via the optical fiber a parallel beam is provided, a directivity may be given to the light beam and the generation of an unnecessary light beam may be avoided. Thus, it is possible to increase the illuminance of the light beam irradiated on the object, and hence an image of high contrast may be obtained.

The objects described above are also achieved by the optical detection device, wherein an irradiation range of the light source device is in correspondence with a length of the groove portion.

According to the above optical detection device, since the irradiation range of the light source device corresponds to the length of the groove portion, it is possible to irradiate the light beam evenly on the entire groove portion.

There is a danger that a reflected light beam may not be surely generated since the morphology of the groove portion is not uniform nor smooth and a lot of concavo-convex portions are formed therein. However, if the irradiation range of the light source device corresponds to the length of the groove portion and the light beam is irradiated evenly on the entire groove portion, it is possible to securely generate the reflected light from the object, and hence the accuracy of an optical detection process may be improved.

The objects described above are also achieved by the optical detection device further comprising: a light moving mechanism continuously changes the irradiation angle of the light beam by moving the light source device.

According to the above optical detection device, since the light moving mechanism which is capable of continuously changing an irradiation angle of the light beam by moving the light source device is provided, the irradiation angle of the light beam may be automatically adjusted using the light moving mechanism.

The objects described above are also achieved by the optical detection device, wherein the light moving mechanism comprises: a base to which at least the camera and the half-mirror are fixed; an arm portion which is rotatably supported by the base and provided with the light source device; and a driving mechanism which rotates the arm portion.

According to the above optical detection device, since the light moving mechanism is comprised of: a base to which at least the camera means and the half-mirror are fixed; an arm portion which is rotatably supported by the base and provided with the light source device; and a driving mechanism which rotates the arm portion, the camera means and the half-mirror may be fixed to a respective predetermined position and the arm portion provided with the light source device may be rotated by the driving mechanism. Thus, the irradiation angle of the light beam from the light source device my be continuously varied with respect to the half-mirror.

Also, since the irradiation angle of the light beam is changed by the driving mechanism, it is possible to automatically adjust the irradiation angle, and hence time required for an optical detection process may be reduced and the efficiency of the process may be improved.

The objects described above are also achieved by the optical detection device, wherein the recognition means comprises: a recognition result storing means for storing the irradiation angle of the light beam from the light source device in relation to a corresponding recognition result of the object every time the irradiation angle is changed; and a selection means for selecting a best recognition result among recognition results stored in the recognition result storing means.

According to the above optical detection device, the recognition result storing means for storing an irradiation angle in relation to a corresponding recognition result every time the irradiation angle is changed is provided together with the selection means for selecting a best recognition result among recognition results. Thus, it is possible to automatically obtain the best irradiation angle of a light beam with respect to an object, and hence the efficiency in recognition of the object may be improved.

The objects described above are also achieved by the optical detection device, wherein the recognition means is in connection with a computer, and the optical detection device further comprises an irradiation angle control means for controlling the irradiation angle of the light beam from the light source device based on information about the object which is supplied from the computer.

According to the above optical detection device, since the recognition means is in connection with an upper computer, and the optical detection device further comprises the irradiation angle control means for controlling the irradiation angle of the light beam from the light source device based on information about the object which is supplied from the upper computer, it becomes possible to control the irradiation angle of the light beam based on the information supplied from the upper computer such as a type or process of an object. Accordingly, there is no need to carry out an operation to find out the best irradiation angle for every object to be detected, and hence the efficiency of an optical detection process is improved.

The objects described above are achieved by a lighting method in an optical detection process in which a recognition process for an object is performed by irradiating a light beam on the object, receiving a reflected light beam from the object by a camera to produce image data, and processing the image data, comprising a step of: carrying out the recognition process by continuously changing an irradiation angle of the light beam irradiated on the object.

According to the above lighting method in the optical detection process, since the recognition process is performed by continuously changing the irradiation angle of the light beam irradiated on the object, an image with high contrast may be obtained for objects of varying shape. Thus, it is possible to carry out an optical detection process with high accuracy.

The objects described above are also achieved by the lighting method in the optical detection process, wherein the object is a groove portion formed on a semiconductor wafer.

According to the above lighting method in the optical detection process, since an image of high contrast can be obtained by continuously changing the irradiation angle as mentioned above, it is possible to detect the groove portion even if the depth of the groove is relatively shallow. Thus, the amount of debris which is produced at the time of the groove formation may be reduced, and the yield of various circuits formed on the semiconductor wafer after the formation of the groove portion may be increased.

The objects described above are also achieved by the lighting method in the optical detection process, wherein the recognition process is performed by continuously changing the irradiation angle of the light beam irradiated on the object after positioning a light source device, a half-mirror, and the object so as to satisfy the equation $L_0=L_1$ where $L_0$ is the distance between the half-mirror and a rotation center of the light source device, and $L_1$ is the distance between the half-mirror and the object using an optical detection device comprising: the light source device from which a light beam is irradiated on the object; an image processing means for receiving a reflected light beam from the object by the camera and producing image data; the half-mirror provided one of between the camera and the object and between the light source device and the object; and a recognition means for carrying out a recognition process of the object based on the image data produced by the image processing means.

According to the above lighting method in the optical detection process, since the light source device, the half-mirror, and the object are provided so as to satisfy the equation $L_0=L_1$, the light beam emitted from the light source device may always be irradiated on the object.

As mentioned above, since the irradiation position may be determined by simply defining the position of the light source device, the half-mirror, and the object so as to satisfy the equation $L_0=L_1$, it is easy to carry out the irradiation position determining process.

Other objects and further features of the present invention will be apparent from the following detailed description when read in conjunction with the accompanied drawings.

DESCRIPTION OF THE PREFERRED EMBODIMENTS

In the following, a principle and embodiments of the present invention will be described with reference to the accompanying drawings.

Figure 3:
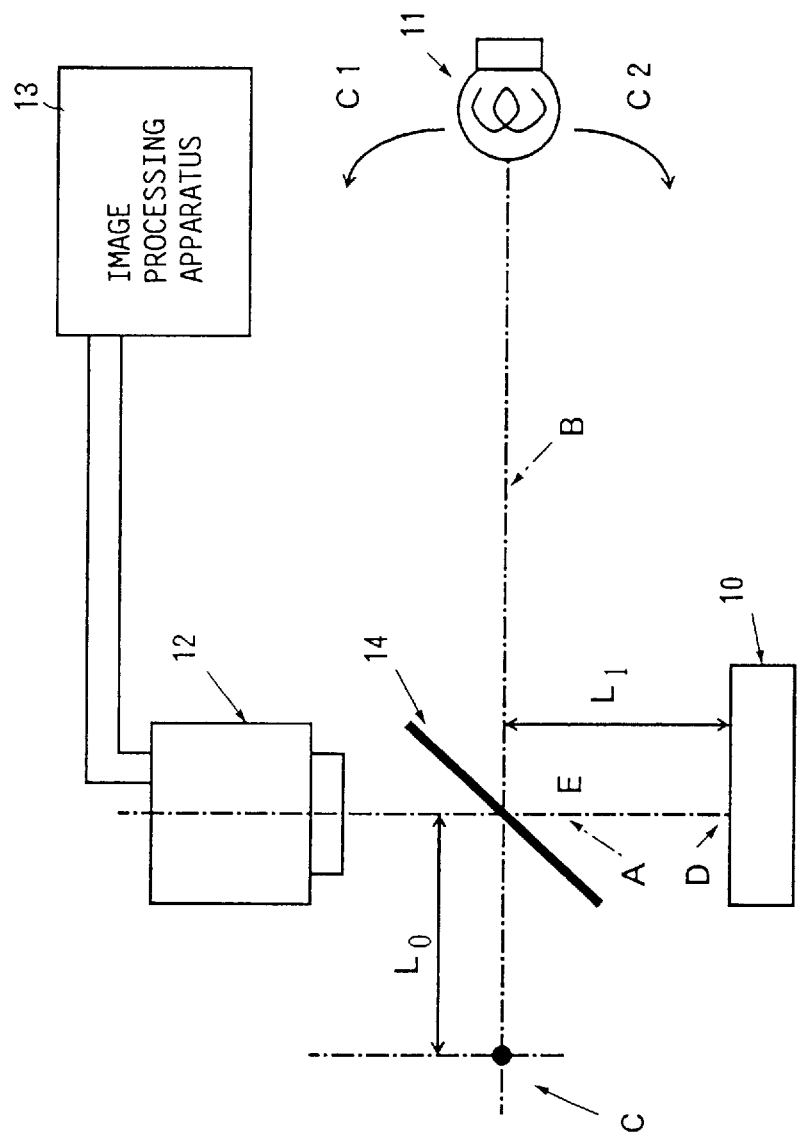
FIG. 3 is a diagram for explaining a principle of the present invention.

FIG. 3 is a diagram showing a principle of the present invention. In the present invention, an image-taking process for an object 10 is basically the same as the conventional one. That is, a light beam from a light source device 11 is irradiated onto the object 10, a reflected light beam from the object 10 is received using a camera means (in this case a CCD) 12 to produce image data, and the image data is processed using an image processing apparatus 13.

The CCD camera 12 is fixed above the object 10 and a half-mirror 14 is provided between the CCD camera 12 and the object 10. The half-mirror 14 is provided at an angle of 45° with respect to an image-taking axis (the dotted line indicated by an arrow A in FIG. 3) of the CCD camera 12.

Figure 1:
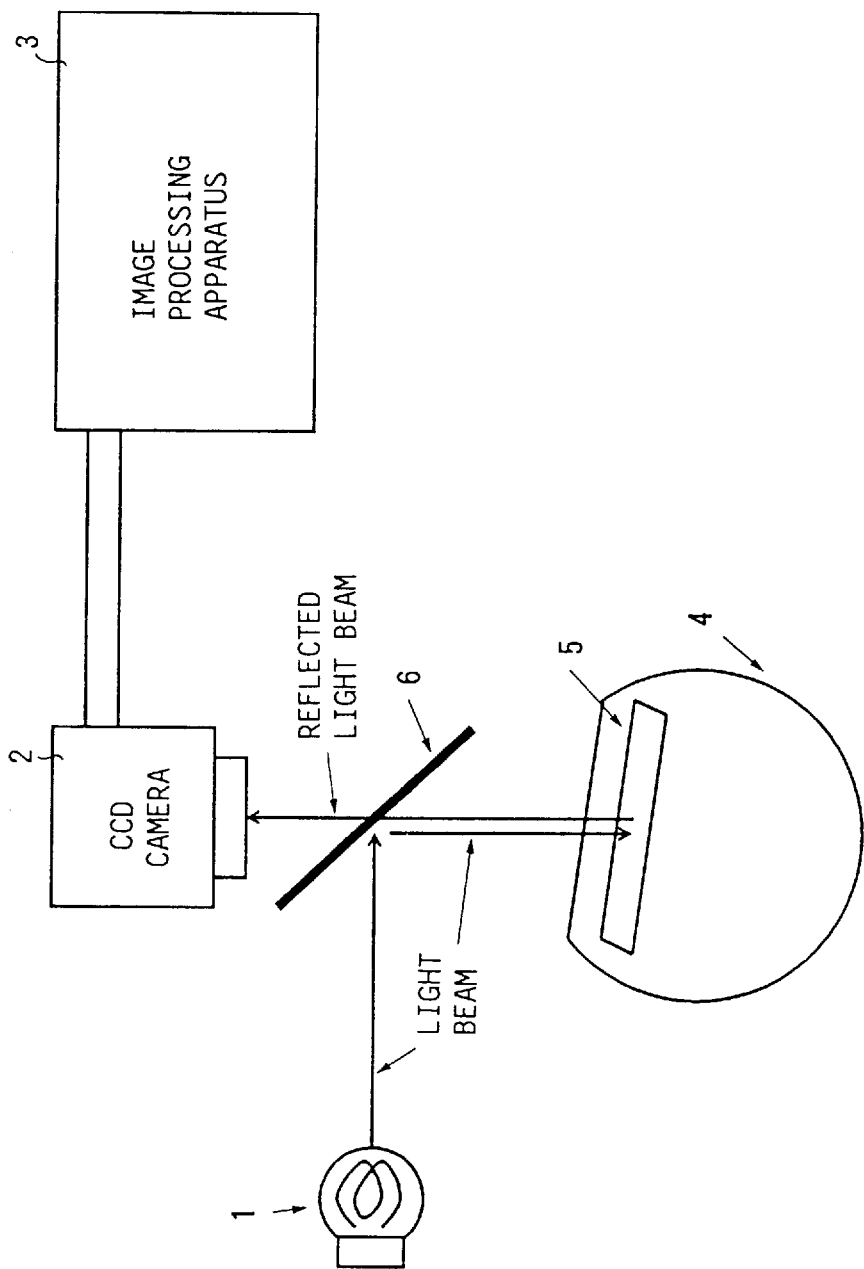
FIG. 1 is a diagram showing a conventional optical detection device using coaxial lighting.
Figure 2:
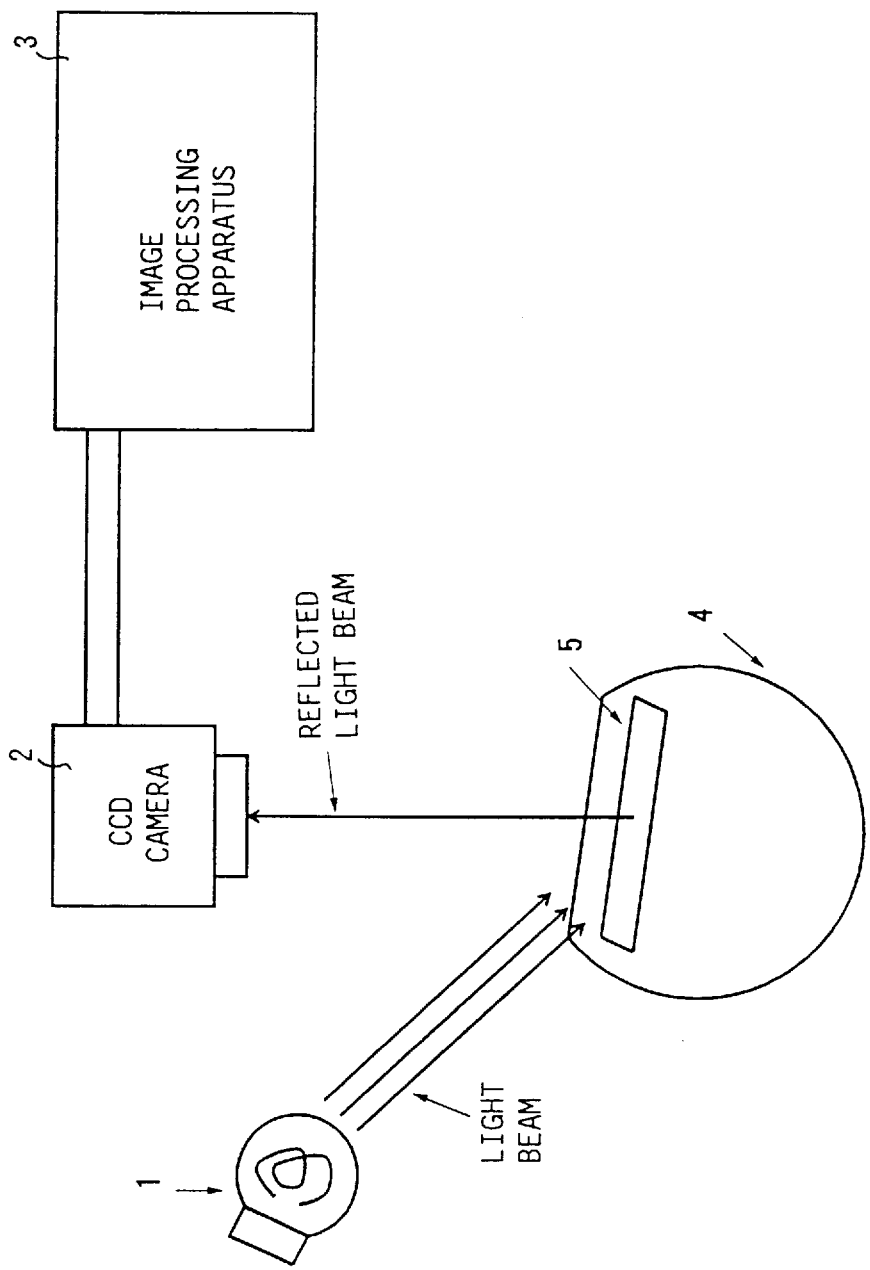
FIG. 2 is a diagram showing a conventional optical detection device using non-coaxial lighting.

Also, the light source device 11 is provided at a position from which a light beam may be irradiated onto the half-mirror 14. Thus, the light beam irradiated from the light source device 11 may be irradiated onto the object 10 via the half-mirror 14. Then, the light reflected by the object 10 passes through the half-mirror 14 and is received by the CCD camera 12 so that image data may be produced. This configuration is similar to the coaxial system shown in FIG. 1.

According to the present invention, however, the irradiation angle of the light beam from the light source device 11 may be continuously changed with respect to the half-mirror 14. That is, the light source device 11 may be continuously rotated in the C1 and C2 directions around a rotation center C shown in FIG. 1 according to the present invention. Suppose that the axis of the light beam irradiated from the light source device 11 is a dotted line indicated by the arrow B in FIG. 1, the light source 11 is rotated with a radius of rotation center C to the light source device 11.

Also, according to the present invention, the light beam, irradiated onto the half-mirror 14 and reflected by the mirror 14, is always focused on the same position (indicated by the arrow D in the figure) of the object 10.

In practice, the position of the object 10, the light source device 11 and the half-mirror 14, respectively, is determined so that $L_0=L_1$ is obtained (wherein Lo is the distance between the rotation center C and the half-mirror 14 and $L_1$ is the distance between the half-mirror 14 and the object 10).

That is, the position of the light source device 11 is determined so that the light beam is irradiated on the half-mirror 14 in the horizontal direction. At that time, the axis of the light reflected by the half-mirror 14 is adjusted so as to be superimposed with the CCD camera axis indicated by the arrow A. In this state, the distance between the point at which the axis of the light beam indicated by the arrow B crosses the half-mirror 14 (indicated by the arrow E, hereinafter referred to as an intersection point E) and the point on the object 10 indicated by the arrow D is defined as $L_1$. Likewise, the distance between the intersection point E and the rotation center C is defined as $L_0$. The positions of the object 10, the light source device 11 and the half-mirror 14 with respect to each other are determined so that $L_0=L_1$ is maintained.

In the above configuration of the present invention, the irradiation angle of the light beam from the light source device 11 may be continuously variable with respect to the half-mirror 14 by rotating the light source device 11 in the C1 and C2 directions around the rotation center C. Thus, it becomes possible to continuously change the irradiation angle of the light beam with respect to the object 10.

According to the present invention, as mentioned above, since it is possible to continuously vary the angle of the light beam with respect to the object 10 using a single light source device 11, images of high contrast may be obtained from the object 10 of varying shape and hence an optical detection process may be achieved with high accuracy. Also, since images of high contrast may be obtained using the single light source device 11, the structure of the light source device 11 and the structure of the entire optical detection device may be simplified.

Moreover, as mentioned above, by locating the object 10, the light source device 11 and the half-mirror 14 so that $L_0=L_1$ is maintained, the light beam irradiated from the light source device 11 and reflected by the half-mirror 14 may be irradiated on the predetermined position D on the object 10 all the time regardless of the position of the light source device 11. For this reason, the light beam is never shifted from the position D of the object 10 when the irradiation angle of the light beam with respect to the position D is continuously varied by the rotation of the light source device 11. Thus, an optical detection process (recognition process) may be performed accurately.

Next, a first embodiment according to the present invention based on the above-mentioned principle will be explained.

Figure 4:
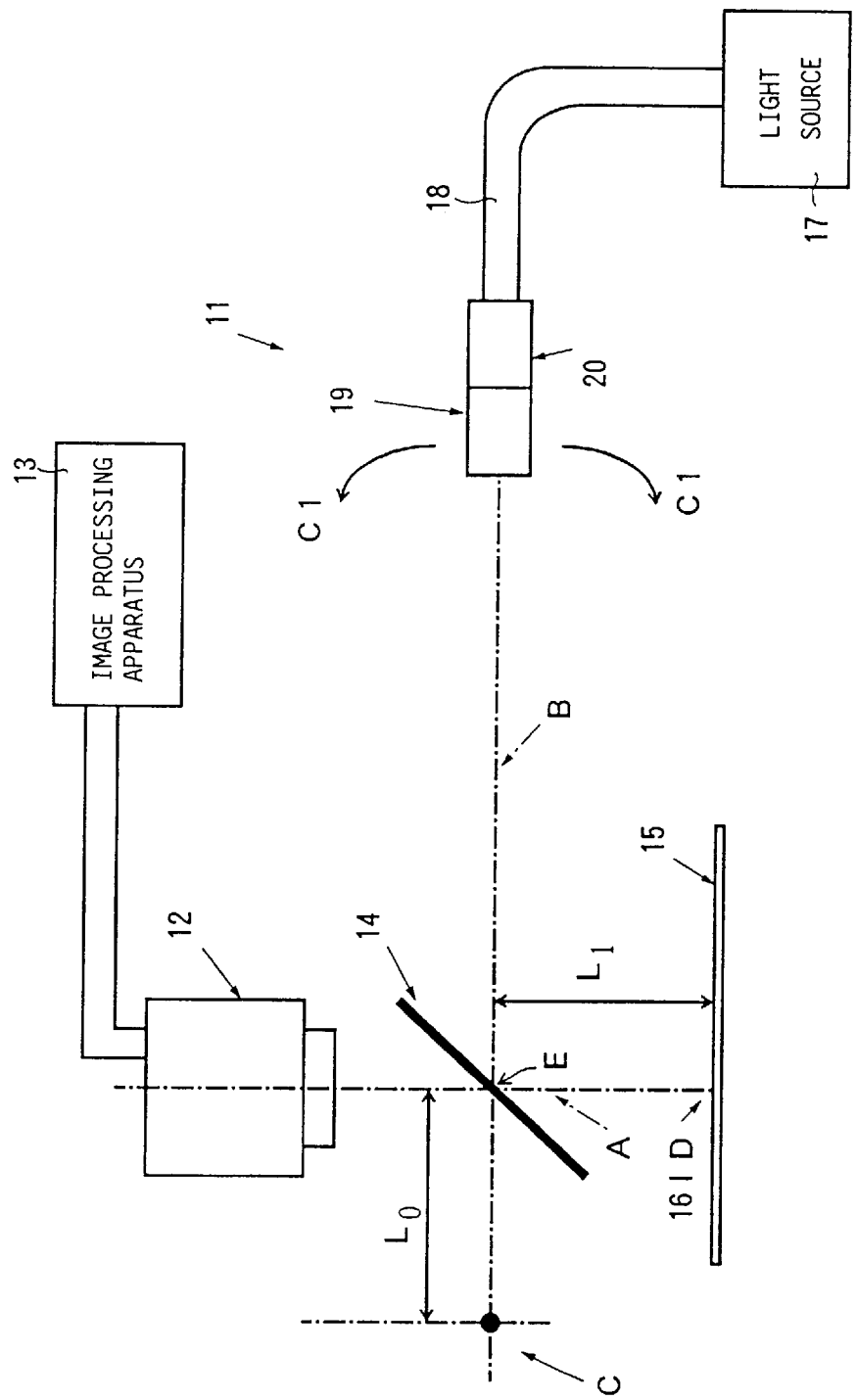
FIG. 4 is a structural diagram of an optical detection device according to a first embodiment of the present invention.
Figure 5:
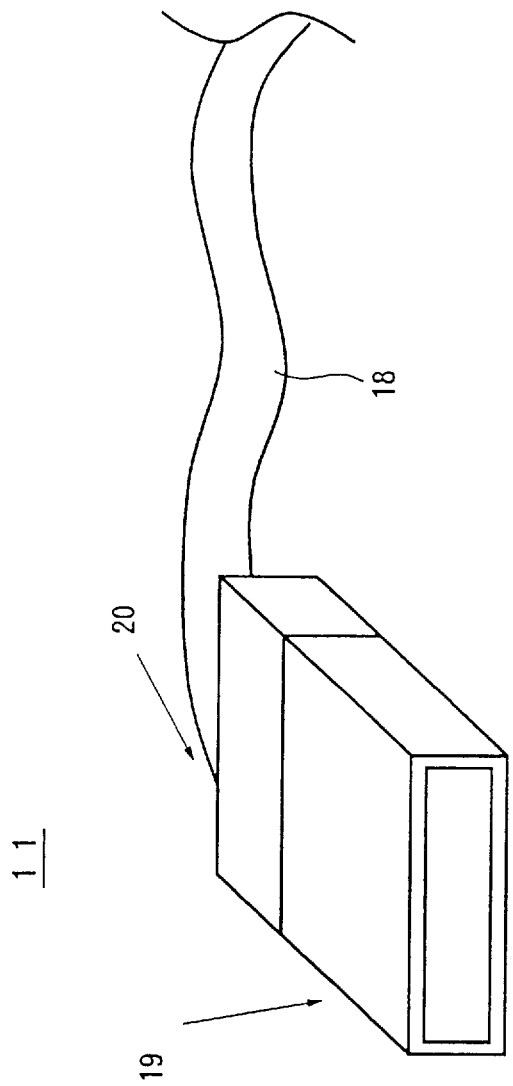
FIG. 5 is a diagram for explaining a condenser unit.
Figure 6:
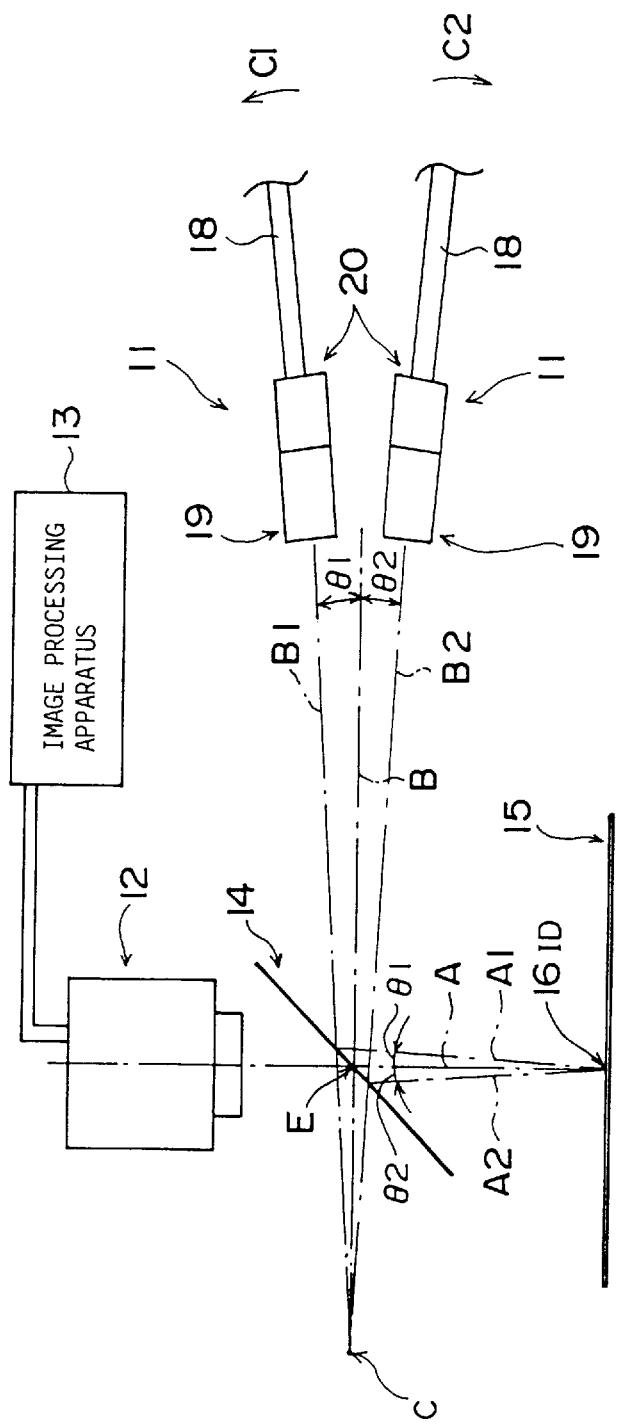
FIG. 6 is a diagram for explaining an operation of the optical detection device according to the first embodiment of the present invention.

FIGS. 4 through 6 are diagrams for explaining an optical detection device according to the first embodiment of the present invention. In FIGS. 4 through 6, elements which are the same as the ones in FIG. 3 are indicated by the same reference numerals. Also, an ID 16 formed on a semiconductor wafer 15 (hereinafter also referred to as a wafer 15) is used as an object 10 to be examined in this embodiment. The ID 16 is comprised of a groove portion formed on the wafer 15.

The optical detection device according to the first embodiment of the present invention is comprised of a CCD camera 12 provided above the wafer 15 so that the camera axis passes through the ID 16, and a half-mirror 14 located between the CCD camera 12 and the wafer 15. The half-mirror 14 is provided so as to cross the camera axis indicated by the arrow A at an angle of 45° with respect to the camera axis.

In this embodiment, the positions of the object 10, the light source device 11 and the half-mirror 14 with respect to each other are also determined so that $L_0=L_1$ is maintained (wherein Lo is the distance between the rotation center C and the half-mirror 14 and $L_1$ is the distance between the half-mirror 14 and the object 10). Thus, the light beam irradiated from the light source device 11 and reflected by the half-mirror 14 may always be irradiated on the ID 16 even when the irradiation angle of the light beam from the light source device 11 with respect to the half-mirror 14 is changed by the rotation of the device 11 (Note that the irradiation angle of the light beam with respect to the ID 16 is varied in accordance with the rotation of the light source device 11).

Next, the light source device 11 used in the embodiment will be explained with reference to FIGS. 4 and 5. FIG. 5 is a diagram showing the light source device 11 in a magnified scale.

The light source device 11 used in the first embodiment of the present invention is comprised of a light source 17, an optical fiber 18, a condenser unit 19, and an optical fiber light guide 20. A halogen lamp having high illuminance is employed as the light source 17. The illuminance of the light source 17 affects the contrast of an image produced, and a higher contrast may be obtained from higher illuminance. Also, the higher the contrast of an image, the more accurate the recognition process. Thus, the halogen lamp is employed as the light source 17 in this embodiment.

The light generated from the light source 17 is supplied to the condenser unit 19 and the optical fiber light guide 20 using the optical fiber 18 in this embodiment. By connecting the condenser unit 19 from which the light beam from the light source 17 is irradiated, it becomes possible to separately provide the condenser unit 19 from the light source 17. In this configuration, a straight light beam having high directivity may be generated.

However, when the condenser unit 19 is located separately from the light source 17, attenuation of the light beam occurs. In this embodiment, therefore, the condenser unit 19 is fixed to a light irradiation inlet so that the light beam from the optical fiber 18 may be condensed and then irradiated onto the ID 16. In this manner, a reduction of illuminance due to the attenuation of the light beam may be prevented and the directivity of the light beam towards the ID 16 may be increased. Thus, a good image contrast may be obtained from the ID 16 having a shallow groove.

Also, according to the embodiment of the present invention, the light source device 11 is constructed so as to be rotatively moved. That is, the condenser unit 19 and the optical fiber light guide 20 move together whereas the light source 17 is fixed. This is due to the presence of the optical fiber 18 connecting the condenser unit 19 with the light source 17, which has a flexible structure. When the condenser unit 19 and the optical fiber light guide 20 move, the optical fiber 18 is capable of deforming its structure so as to follow the movement of the condenser unit 19 and the optical fiber light guide 20. Therefore, the light from the light source 17 may be stably supplied to the condenser unit 19. In addition, the optical fiber light guide 20 functions as an optical connector which connects the optical fiber 18 which the condenser unit 19.

The wafer ID 16 used in this embodiment of the present invention is comprised of a plurality of character codes aligned horizontally. Thus, the ID 16 has a predetermined length. For this reason, according to the embodiment of the present invention, the irradiation range of the condenser unit 19 is adjusted so as to correspond to the length of the ID 16 which is formed by groove portions. That is, the irradiation range of the condenser unit 19 is substantially the same as the length of the ID 16. Also, the width of the optical fiber light guide 20 is adjusted so as to correspond to the irradiation range of the condenser unit 19.

In the above-mentioned structure of the light source device 11, it is possible to evenly irradiate the entire ID 16 (i.e., the groove portions) with the light beam. If the entire ID 16 is not uniformly irradiated and only a part of the ID 16 is irradiated, there is a danger that the reflected light beam may not be surely generated since the groove portions of the ID 16 are not uniform nor smooth and a lot of concavo-convex portions are formed therein.

As mentioned above, since the irradiation range of the condenser unit 19 is adjusted so as to correspond to the length of the ID 16, the entire ID 16 may be evenly irradiated and hence the reflected light beam may be securely generated. Accordingly, the accuracy of an optical detection process may be improved. Also, an image of high contrast may be obtained even from an ID which is formed of a shallow groove portion and is hard to recognize by a conventional lighting method.

Moreover, according to the present invention, the light source device 11 may be formed of a plurality of optical fibers 18, a plurality of condenser units 19 and a plurality of optical fiber light guides 20. By using the plurality of optical fibers 18, condenser units 19 and optical fiber light guides 20, it is possible increase the illuminance of the light beam irradiated on the ID 16, and hence the contrast of an image obtained may be improved.

Next, operation of the optical detection device having the above-mentioned structure according to the first embodiment of the present invention will be explained with reference to FIG. 6. Since the characteristic of the present invention lies in the light source device 11, only the operation of the light source device 11 will be described.

FIG. 6 is a diagram for explaining a state of the optical detection device when the condenser unit 19 is rotated in the C1 direction or in the C2 direction.

When the condenser unit 19 is rotated in the C1 direction at a predetermined angle θ1 around the rotation center C from the state shown in FIG. 4 (hereinafter also referred to as a standard state), the light beam irradiated from the condenser unit 19 passes through the optical axis B1 and reaches the half-mirror 14. The light beam is then reflected by the half-mirror 14 so as to pass through the optical axis A1 and irradiated on the ID 16.

On the other hand, when the condenser unit 19 is rotated in the C2 direction at a predetermined angle θ2 around the rotation center C from the standard state, the light beam irradiated from the condenser unit 19 passes through the optical axis B2 and reaches the half-mirror 14. The light beam is then reflected by the half-mirror 14 so as to pass through the optical axis A2 and irradiated on the ID 16.

Here, the irradiation of the ID 16 with the reflected light beam from the half-mirror 14 will be explained in detail. In the standard state shown in FIG. 4, the light beam is projected to the half-mirror 14 horizontally from the condenser unit 19. Since the half-mirror 14 is provided at an angle of 45° with respect to the vertical direction, the light beam reflected by the half-mirror 45 is irradiated on the ID 16 in the vertical direction with respect to the surface of the wafer 15. That is, the light beam is irradiated along the camera axis A.

On the other hand, when the condenser unit 19 is rotated in the C1 direction at the predetermined angle θ1 around the rotation center C from the standard state, the light beam reflected by the half-mirror 45 is irradiated on the ID 16 in a direction inclined at the angle θ1 with respect to the camera axis A. Also, when the condenser unit 19 is rotated in the C2 direction at the predetermined angle θ1 around the rotation center C from the standard state, the light beam reflected by the half-mirror 45 is irradiated on the ID 16 in a direction inclined at the angle θ2 with respect to the camera axis A.

That is, by using the optical detection device according to the embodiment of the present invention, the irradiation angle may be continuously changed, without stopping the irradiation of the light beam on the ID 16, by rotating the condenser unit 19 in the C1 direction or C2 direction from the standard state.

Thus, it becomes possible to irradiate the ID 16 in the most appropriate direction at a suitable irradiation angle, and hence an image with high contrast may be obtained according to the present invention.

Figure 7:
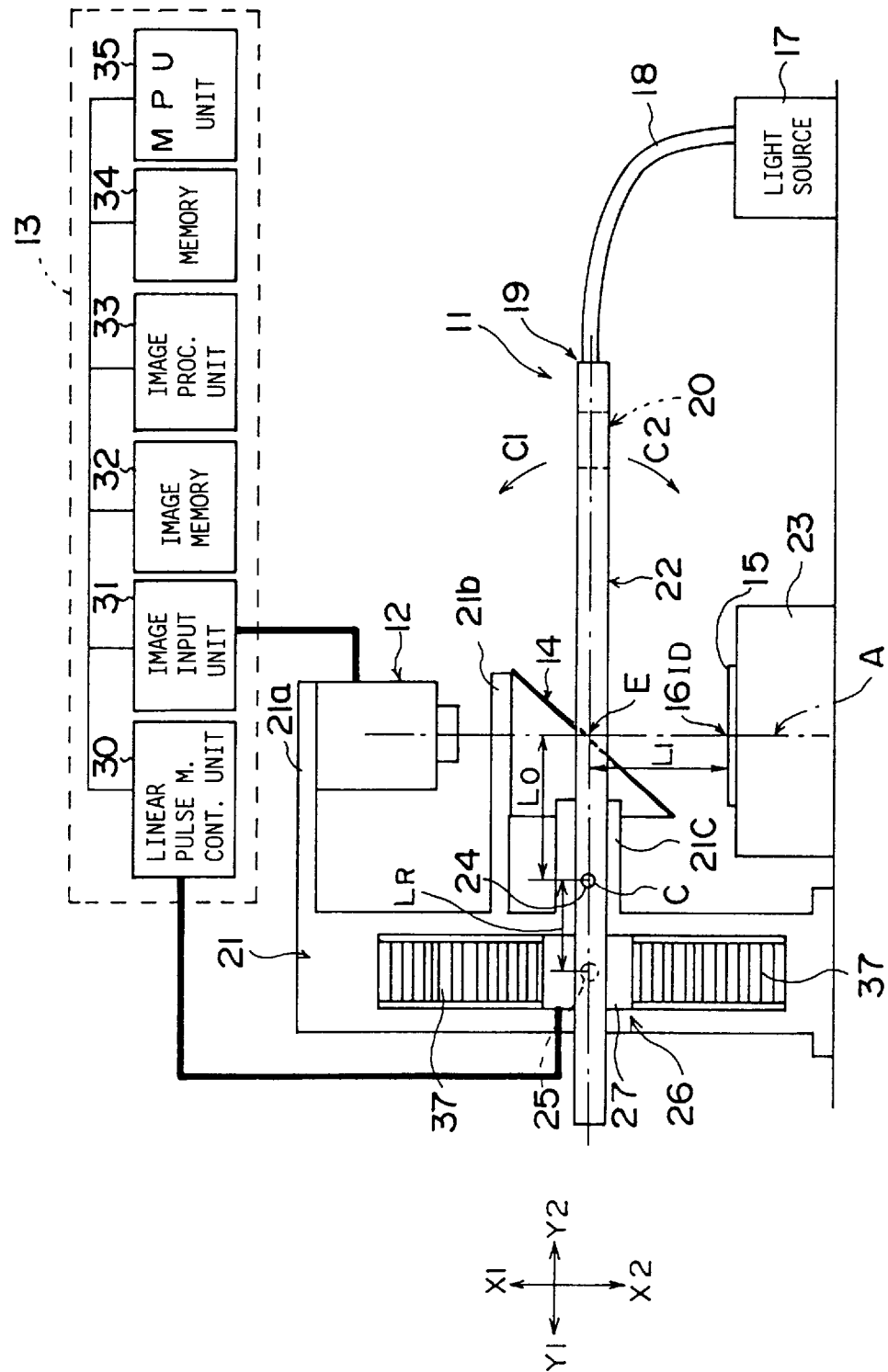
FIG. 7 is a diagram showing an optical detection device according to a second embodiment of the present invention.
Figure 8:
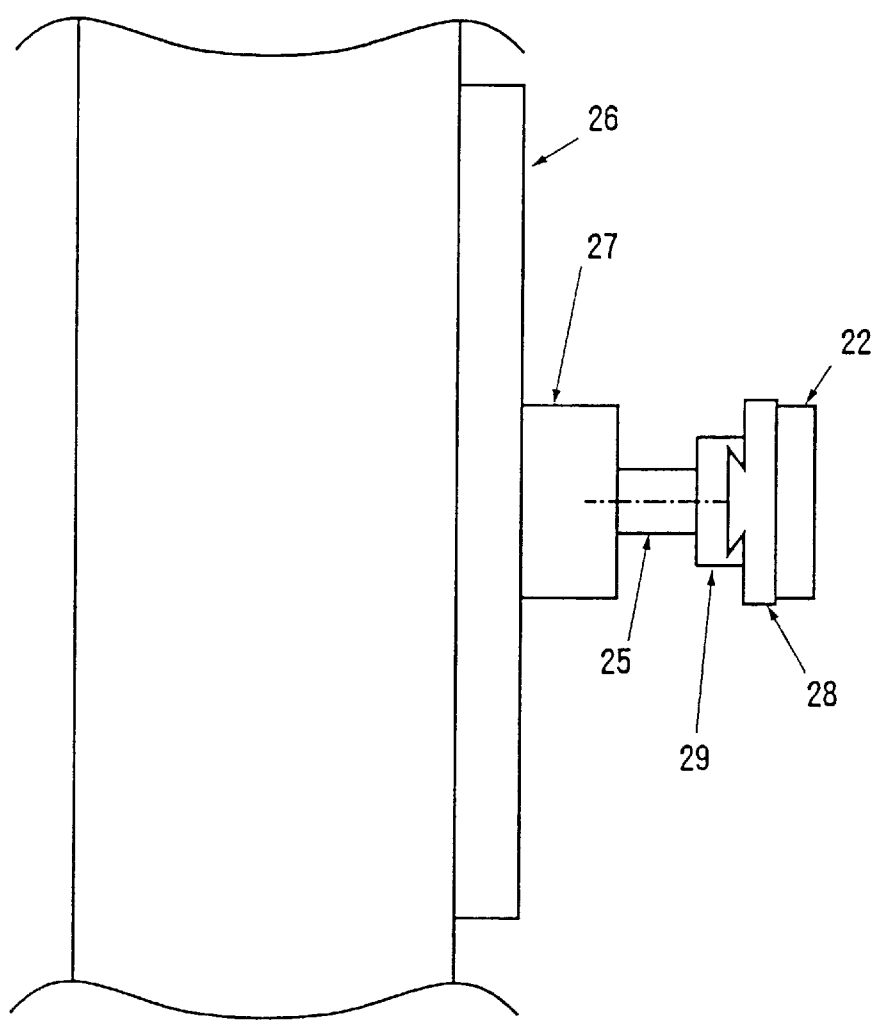
FIG. 8 is a diagram showing the optical detection device shown in FIG. 7 from the left-hand side.

Next, an optical detection device according to a second embodiment of the present invention will be described with reference to FIGS. 7 through 10. In FIGS. 7 and 8, elements which are the same as the ones in FIGS. 3 through 6 are indicated by the same reference numerals and the explanation thereof will be omitted.

The optical detection device shown in FIG. 7 is a concrete embodiment of the first embodiment shown in FIG. 4. In FIG. 7, a control system is also shown together with the optical detection device. FIG. 8 is a diagram showing the optical detection device shown in FIG. 7 from the left-hand side.

As shown in FIG. 7, a base 21 includes three extending portions 21a, 21b and 21c from the top. A CCD camera 12 is fixed to the extending portion 21a downwardly and a half-mirror 14 is fixed to the extending portion 21b so as to be inclined at 45° with respect to the camera axis A.

A mount 23 for mounting the wafer 15 is provided in the downward direction of the CCD camera 12 and the half-mirror 14. When the wafer 15 is mounted on the mount 23, the wafer 15 is positioned so that the ID 16 formed on the wafer 15 is aligned with the center of the camera axis of the CCD camera 12.

On the other hand, an arm 22 is provided with the extending portion 21c. The arm 22 is a square rod member and the condenser unit 20 and the optical fiber light guide 19 of the light source device 11 are fixed to the right-hand side end thereof.

The arm 22 is rotatably supported by a rotary shaft 24, and hence the arm 22 may be rotated around the rotary shaft 24. Accordingly, the light source device 11 (i.e., the optical fiber light guide 19 and the condenser unit 20) may be rotated around the rotary shaft 24.

The position of the half-mirror 14, the wafer 15 and the rotary shaft 24 may be adjusted as follows. Firstly, the position of the arm 22 is determined so that the light beam may be irradiated horizontally to the half-mirror 14 from the light source device 11 (i.e., the condenser unit 20) and the axis of the reflected light from the half-mirror 14 is aligned with the camera axis A.

Then, the position of the rotary shaft 24 is determined so that $L_0 = L_1$ is achieved (wherein $L_0$ is the distance between an intersection point E and the rotary shaft 24 which is a rotation center C of the light source device 11, and $L_1$ is the distance between the intersection point E and the ID 16 formed on the wafer 15, the intersection point E being a point at which the axis B of the light beam irradiated from the light source device 11 crosses the half-mirror 14).

According to the above-explained construction, the light source device 11 may be rotated around the rotary shaft 24 (the rotation center C) when the arm 22 is rotated around the rotary shaft 24. Therefore, it becomes possible to continuously change the irradiation angle of the light beam with respect to the ID 16 as shown in FIG. 6.

Next, a light moving mechanism which changes the angle of the light beam irradiated on the ID 16 by moving the light source device 11 will be explained. The light moving mechanism rotates the arm 22 by a linear pulse motor 26 so as to continuously move the light source device 11.

The linear pulse motor 26 is comprised of a link portion 25 and a linear pulse motor driving portion 27. One end of the link portion 25 is rotatably connected to the linear pulse motor driving portion 27 and the other end of the link portion 25 is rotatably connected to the arm 22. The position at which the link portion 25 is connected to the arm 22 is located at the left-hand side of the rotary shaft 24 as shown in FIG. 7.

The linear pulse motor driving portion 27 is engaged with a rail portion 37 which extends in an up-and-down direction from the base 21. The linear pulse motor driving portion 27 moves linearly in the directions indicated by the arrows X1 and X2 when receiving a signal from an image processing apparatus 13 which will be described in detail later.

Suppose that the linear pulse motor driving portion 27 is moved in the direction indicated by the arrow X1 (i.e., the upward direction in FIG. 7, hereinafter also referred to as an X1 direction), the link portion 25 which is connected to the linear pulse motor driving portion 27 is also moved in the X1 direction. Hence, the arm 22 is rotated in the direction indicated by the arrow C2. Accordingly, the light source device 11 (the condenser unit 20) which is fixed to the right end of the arm 22 is also rotated in the direction indicated by the arrow C2.

On the other hand, suppose that the linear pulse motor driving portion 27 is moved in the direction indicated by the arrow X2 (i.e., the downward direction in FIG. 7, hereinafter also referred to as an X2 direction), the link portion 25 is also moved in the X2 direction. Hence, the arm 22 is rotated in the direction indicated by the arrow C1. Accordingly, the light source device 11 (the condenser unit 20) is also rotated in the direction indicated by the arrow C1.

The linear pulse motor 26 used in this embodiment is constructed so that a minimum transfer distance of the linear pulse motor driving portion 27 during a driving state becomes sufficiently short. Thus, it is possible to substantially continuously rotate the arm 25 and to stop the arm 25 so as to obtain a desirable angle thereof.

Now, when the linear pulse motor driving portion 27 is moved in the X1 or X2 direction guided by the rail portion 37, the distance between the rotary shaft 24 and the link portion 25 (indicated by an arrow $L_R$ in FIG. 7) is changed. Thus, if a structure of the device in which the distance $L_R$ between the rotary shaft 24 and the link portion 25 is fixed is used, it is not possible to move the linear pulse motor driving portion 27.

For this reason, according to this embodiment, a guide rail 28 and a guide rail driving portion 29 are provided with the arm 22 as shown in FIG. 8. In this configuration, the guide rail 28 expands along the arm 22 by the guide rail driving portion 29. Thus, when the distance $L_R$ between the rotary shaft 24 and the link portion 25 is changed due to the movement of the linear pulse motor driving portion 27, the change may be absorbed by the displacement of the guide rail 28 with respect to the arm 22. In this manner, the smooth rotating operation of the arm 25 may be obtained.

Next, the image processing apparatus 13 provided with the optical detection device will be explained.

The image processing apparatus 13 is comprised of a linear pulse motor control unit 30, an image input unit 31, an image memory 32, an image processing unit 33, memory 34, and a central control unit (MPU unit) 35.

The linear pulse motor control unit 30 is connected to the linear pulse motor 26 and controls the operation of the linear pulse motor 26 based on an order from the MPU unit 35 (to be described later). Also, the image input unit 31 is connected to the CCD camera 12 and generates image data based on the camera signals supplied from the CCD camera 12.

The image memory 32 functions so as to store the image data supplied from the image input unit 31. Also, the memory 34 stores various programs, which are necessary when carrying out an optical detection process, results of a recognition process which is necessary for performing a wafer ID recognition process to be described later, and so on.

The MPU unit functions so as to carry out the wafer ID recognition process based on the image data, etc., which is stored in the image memory 32. The image memory 32 and the MPU unit 35 function together so as to construct the above-mentioned recognition means. Also, the image memory 32 constructs the above-mentioned recognition result storing means.

Now, since the optical detection device is used in a semiconductor production line, the yield of the semiconductor device would be lowered if the recognition process of the ID 16 by the optical detection device is slow. Therefore, it is necessary to improve the efficiency of the ID 16 recognition process in the optical detection device.

On the other hand, as mentioned above, the optical detection device according to the present invention has a structure in which the angle of the light beam irradiated on the ID 16 from the light source device 11 may be changed. The change of the angle is possible within the predetermined range (hereinafter one end of the range is referred to as an initial value and the other end of the range is referred to as a limit value). However, if a recognition process is performed by changing the irradiation angle over the entire predetermined range (i.e., from the initial value to the limit value) for all the wafer 15 to be examined (i.e., all the wafer 15 to be produced), a significant amount of time is required for the optical detection process and the efficiency of the process is lowered.

According to the embodiment of the present invention, therefore, a kind of study function is given to the optical detection device. That is, in the recognition process, a particular irradiation angle of the light beam, by which a best recognition result (i.e., an image having high contrast) is obtained, is stored in the memory so that the data may be used in the next recognition process. Thus, according to the embodiment of the present invention, an irradiation angle of the light beam may be automatically adjusted so as to obtain the best condition for the ID recognition. Hence, the efficiency of the optical detection process may be improved according to the present invention.

Next, the wafer ID recognition process (the optical detection process) carried out in the embodiment according to the present invention will be explained.

Figure 10:
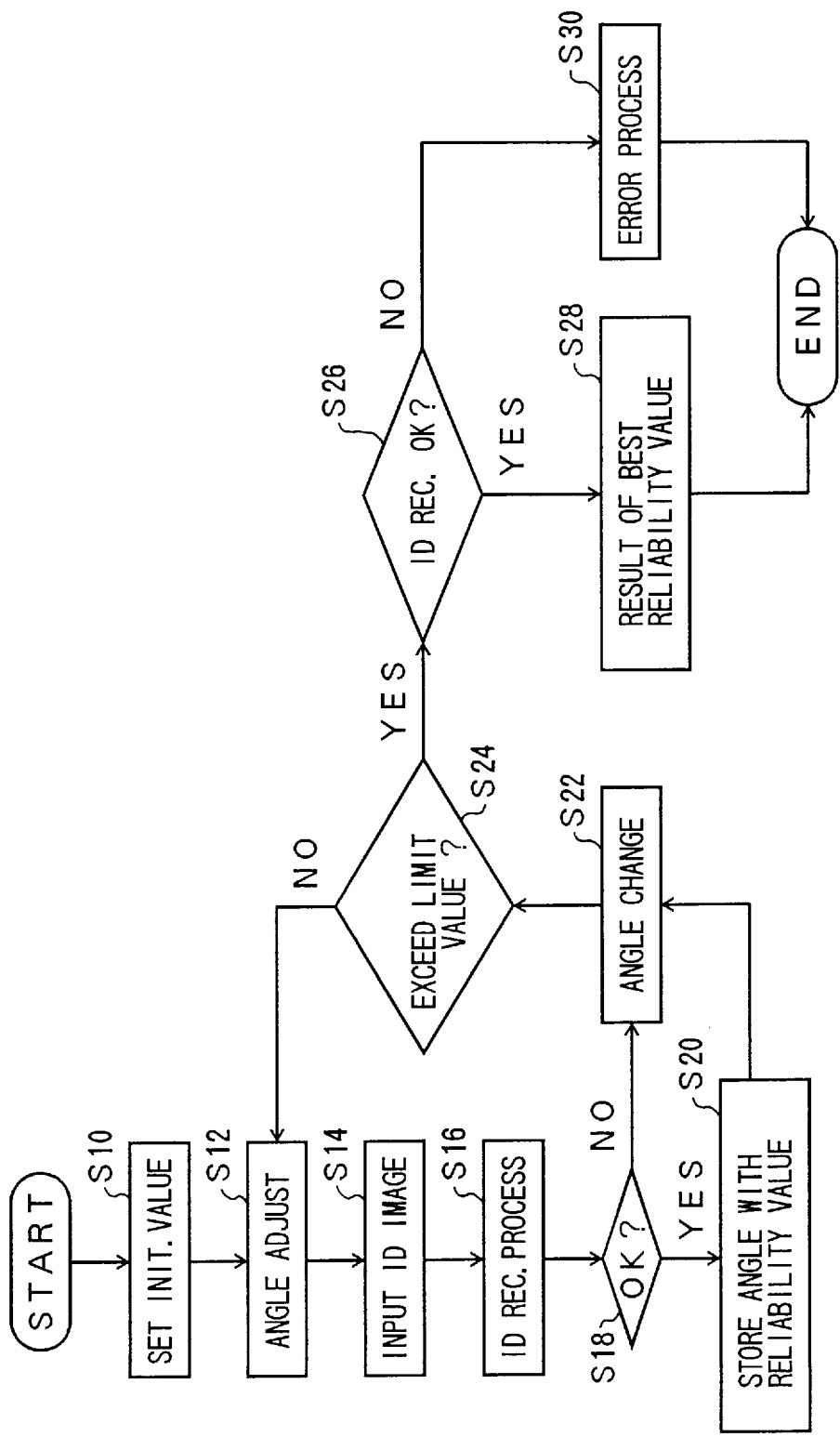
FIG. 10 is a diagram showing a flowchart for an ID recognition process with an optimal irradiation angle.

FIG. 10 is a diagram showing a flowchart of the wafer ID recognition process. A program for the wafer ID recognition process is stored in the memory 34 of the image processing apparatus 13.

As shown in FIG. 10, when the wafer ID recognition process is started, an initial value and a limit value of the irradiation angle (i.e., the irradiation range) are set in step 10 (S10). At the same time, an interval angle within the irradiation range (i.e., the angle change between each irradiation operation) is determined. The values set in this step are stored in the memory 34.

In step 12 (S12), the MPU unit 35 supplies signals to the linear pulse motor control unit 30 so that the irradiation angle is adjusted to the initial value. The linear pulse motor control unit 30 drives the linear pulse motor 26 based on the signal supplied from the MPU unit 35. Thus, the arm 22 is rotated so as to rotate the condenser unit 20 of the light source device 11 to the position where the irradiation angle matches the initial value.

On the other hand, as mentioned above, it is necessary to supply the signal indicating the moving distance, not the angle, to the linear pulse motor 26 since the linear pulse motor 26 moves the link portion 25, which is connected to the arm 22, in the X1 and the X2 directions (refer to FIG. 7). Thus, it is necessary to calculate the transfer distance δh of the link portion 25 by the linear pulse motor 26 from the indicated irradiation angle θ.

Figure 9:
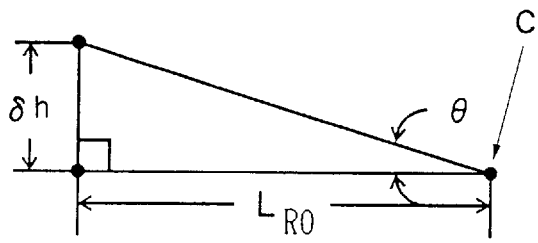
FIG. 9 is a diagram for explaining a method for obtaining an irradiation angle of a light beam.

FIG. 9 is a diagram for explaining the calculation of the transfer distance δh.

Referring to FIG. 9, the irradiation angle θ of a light beam may be calculated by the equation:

$$\theta = \text{Tan}^{-1}(\delta h / L_{RO}) \quad (1)$$

(where $L_{RO}$ is a distance between the rotary shaft 24 and the link portion 25 and δh is a transfer distance of the link portion 25 by the linear pulse motor 26.)

Therefore, the transfer distance δh may be expressed as:

$$\delta h = \text{Tan } \theta \times L_{RO} \quad (2)$$

Thus, δh may be calculated from the given irradiation angle θ and the result may be supplied to the linear pulse motor control unit 30 as a signal from the MPU unit 35 to achieve the irradiation angle θ.

As shown in FIG. 10, when a signal is sent to the linear pulse motor control unit 30 so that the irradiation angle is adjusted to the initial value in step 12, the MPU unit 35 sends a signal to the image input unit 31 in step 14 so that data of an image taken by the CCD camera 12 (hereinafter also referred to as an ID image) may be input. The input ID image is stored in the image memory 32.

In step 16, a signal is supplied to the image processing unit 33 from the MPU unit 35 so that a recognition process of the ID 16 formed on the wafer 15 may be performed. When the recognition process is completed, the result is supplied to the MPU unit 35 from the image processing unit 33.

On occasion, there is a possibility that the recognition of the ID 16 may fail. Thus, in step 18, it is determined if the recognition of the ID 16 is successful or not. If it is not successful, the MPU unit 35 supplies a signal to the linear pulse motor control unit 30 so that the angle of the light beam is changed for the next irradiation in step 22.

In step 24, it is determined if the angle of the light beam changed in step 22 by the MPU 35 is within the predetermined irradiation range (i.e., not exceeding the limit value). If it is determined that the angle is within the predetermined range, the process goes back to step 12.

On the other hand, when it is determined that the recognition of the ID 16 is successful in step 18, the process goes to step 20. In practice, there are two cases for the successful recognition—one is that the recognition is clear and the other is that the recognition is unclear. Naturally, the reliability of the ID recognition process is increased when the recognition is clear.

For the above reason, the result of the recognition supplied to the MPU unit 35 in step 16 includes the information about the ID recognition with a mathematical value (reliability value) which indicates the reliability of the recognition. The larger the mathematical value, the more accurate the recognition. In step 20, the result of the recognition is stored in the memory 34 together with the irradiation angle θ.

After the completion of step 20, the process goes to steps 22 and 24, and if it is determined that the irradiation angle is within the predetermined range, the process goes back to step 12. That is, step 12 through step 24 are carried out repeatedly so as to cover the entire predetermined range.

Next, a case in which it is determined that the irradiation angle is not within the predetermined range (i.e., over the limit value) in step 24 will be explained.

When it is determined that the irradiation angle exceeds the limit value in step 24, the process goes to step 26. In step 26, it is determined whether the ID 16 is recognized during the steps 12 through 24. If it is determined that the ID is not recognized even once in step 26, then the process goes to step 30 in which an error process is carried out. That is, a state in which no ID recognition is carried out is the state in which no information about the wafer 15 is obtained, and hence processes (semiconductor manufacturing process) supposed to be performed after the recognition process can not be performed. Thus, information is provided that the wafer 15 is in an erroneous state in step 30 and the error process such as a process in which the wafer 15 is taken out from the semiconductor production line is carried out.

On the other hand, when it is determined that the ID recognition is performed in step 26, the process goes to step 28. In step 28, the result of the recognition having the largest reliability value recorded in the memory 34 is regarded as the result of the recognition for the ID 16. Also, the irradiation angle from which the best result of the ID 16 recognition is obtained is stored in the memory 34. In this manner, it is possible to perform a recognition process for the ID 16 with the best irradiation angle using the stored information. Accordingly, the process for adjusting the irradiation angle may be omitted, and hence the efficiency of the recognition process may be improved.

Figure 11:
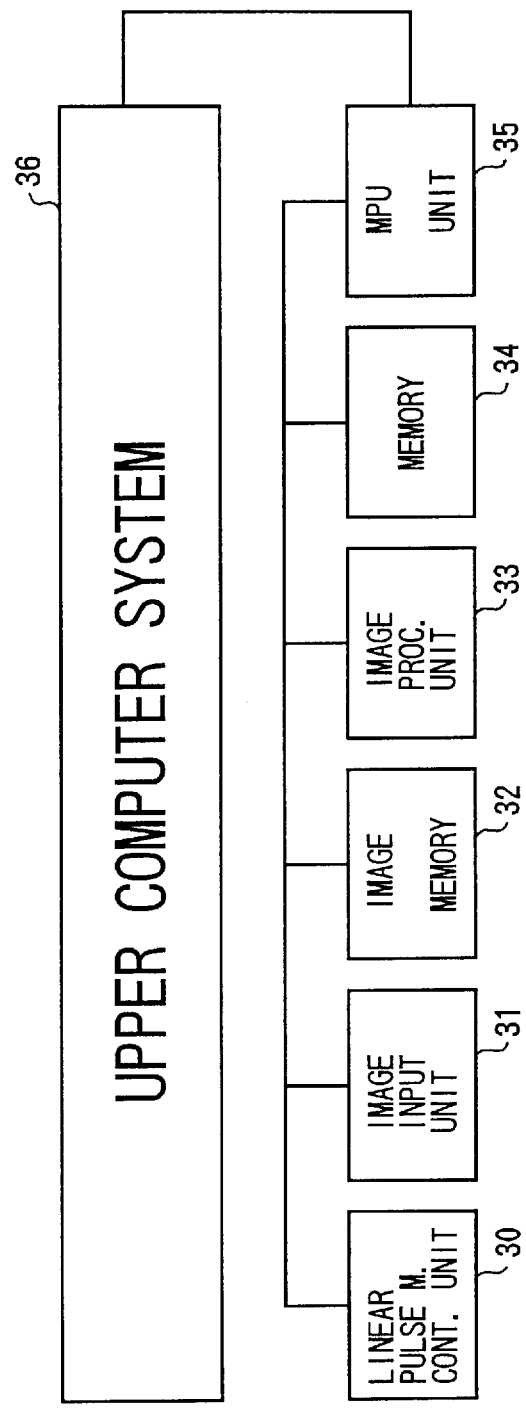
FIG. 11 is a diagram showing a structure of the present invention when connected to an upper computer system.

FIG. 11 is a structural diagram showing the image processing apparatus 13 and an upper computer system 36 having the information about the wafer 15.

In the configuration shown in FIG. 11, the MPU unit 35 is connected to the upper computer system 36, and hence communication can be made therebetween. The MPU unit 35 receives information of the ID 16 and the wafer 15 provided with the ID 16 (hereinafter the information is also referred to as wafer ID information) and a recognition order signal from the upper computer system 36.

The wafer ID information includes information about the production of the ID 16, the processes the wafer 15 has undergone and so on. Thus, in the embodiment having the configuration shown in FIG. 11, the MPU unit 35 retrieves the irradiation angle from which the best image may be obtained from the data of the condition for the irradiation angle stored in the memory 34 and immediately supplies signals to adjust the angle and starts the recognition process.

In this manner, it is not necessary to carry out an operation for determining the best irradiation angle by changing the angle of the light beam every time. Accordingly, the efficiency of the recognition process may be improved. Also, it becomes possible to store the conditions of the irradiation angle in a memory located in the upper computer system 36 and supply the signal to change the irradiation angle directly to the MPU unit 35 from the upper computer system 36. Thus, the load of the memory 34 may be reduced.

Moreover, in each of the above-mentioned embodiments, the CCD camera 12 is located above the half-mirror 14 and the light source device 11 is provided so as to be movable in the transverse directions with respect to the half-mirror 14.

However, the position of the light source device 11, the CCD camera 12 and the half-mirror 14 are not limited as above and, for example, the position of the light source device 11 may be switched to that of the CCD camera 12 so that the light source device 11 is movably located above the half-mirror 14 and the CCD camera 12 is located at one side of the half-mirror 14. In such a case, the light beam irradiated from the light source device 11 passes through the half-mirror 14 and is irradiated on the ID 16.

It is obvious that the present invention is not limited to the above-mentioned embodiments, and variations and modifications may be made without departing from the scope of the present invention.

What is claimed is:

1. An optical detection device comprising:

a light source device from which a light beam is irradiated on an object;

an image processing means for receiving a reflected light beam from said object by a camera and producing image data;

a half-mirror provided one of between said camera and said object and between said light source device and said object; and a recognition means for carrying out a recognition process of said object based on said image data produced by said image processing means, wherein an irradiation angle of said light beam from said light source device is continuously varied with respect to said half-mirror, and said light beam from said light source device is always irradiated on said object via said half-mirror.

2. The optical detection device as claimed in claim 1, wherein said object is a groove portion formed on a semiconductor wafer.

3. The optical detection device as claimed in claim 1, wherein said light source device, said half-mirror, and said object are positioned so as to satisfy an equation $L_0=L_1$ where $L_0$ is the distance between said half-mirror and a rotation center of said light source device, and $L_1$ is the distance between said half-mirror and said object.

4. The optical detection device as claimed in claim 1, wherein said light source device is in connection with a light source via an optical fiber, and said light source device is provided with an optical system makes a light beam supplied via said optical fiber a parallel beam.

5. The optical detection device as claimed in claim 2, wherein an irradiation range of said light source device is in correspondence with a length of said groove portion.

6. The optical detection device as claimed in claim 1 further comprising:

a light moving mechanism continuously changes said irradiation angle of said light beam by moving said light source device.

7. The optical detection device as claimed in claim 6, wherein said light moving mechanism comprises:

a base to which at least said camera and said half-mirror are fixed;

an arm portion which is rotatably supported by said base and provided with said light source device; and a driving mechanism which rotates said arm portion.

8. The optical detection device as claimed in claim 1, wherein said recognition means comprises:

a recognition result storing means for storing said irradiation angle of said light beam from said light source device in relation to a corresponding recognition result of said object every time said irradiation angle is changed; and a selection means for selecting a best recognition result among recognition results stored in said recognition result storing means.

9. The optical detection device as claimed in claim 1, wherein said recognition means is in connection with a computer, and said optical detection device further comprises an irradiation angle control means for controlling said irradiation angle of said light beam from said light source device based on information about said object which is supplied from said computer.

10. A lighting method in an optical detection process in which a recognition process for an object is performed by irradiating a light beam on said object, receiving a reflected light beam from said object by a camera to produce image data, and processing said image data, comprising a step of:

carrying out said recognition process by continuously changing an irradiation angle of said light beam irradiated on said object.

11. The lighting method in the optical detection process as claimed in claim 10, wherein said object is a groove portion formed on a semiconductor wafer.

12. The lighting method in the optical detection process as claimed in claim 10, wherein said recognition process is performed by continuously changing said irradiation angle of said light beam irradiated on said object after positioning a light source device, a half-mirror, and said object so as to satisfy the equation $L_0=L_1$ where $L_0$ is the distance between said half-mirror and a rotation center of said light source device, and $L_1$ is the distance between said half-mirror and said object using an optical detection device comprising:

said light source device from which a light beam is irradiated on said object;

an image processing means for receiving a reflected light beam from said object by said camera and producing image data;

said half-mirror provided one of between said camera and said object and between said light source device and said object; and a recognition means for carrying out a recognition process of said object based on said image data produced by said image processing means.

\* \* \* \* \*